United States Patent
Hildreth

(12) 
(10) Patent No.: US 6,187,308 B1
(45) Date of Patent: Feb. 13, 2001

(54) MONOCLONAL ANTIBODIES AGAINST LEUKOCYTE ADHESION RECEPTOR β-CHAIN, METHODS OF PRODUCING THESE ANTIBODIES AND USE THEREFOR

(75) Inventor: James E. Hildreth, Baltimore, MD (US)

(73) Assignee: The Johns Hopkins University School of Medicine, Baltimore, MD (US)

(*) Notice: Under 35 U.S.C. 154(b), the term of this patent shall be extended for 0 days.

(21) Appl. No.: 09/197,318

(22) Filed: Nov. 20, 1998

Related U.S. Application Data

(62) Division of application No. 08/598,095, filed on Feb. 7, 1996, now Pat. No. 5,888,508, which is a continuation of application No. 08/200,491, filed on Feb. 22, 1994, now abandoned, which is a division of application No. 08/063,063, filed on May 20, 1993, now abandoned, which is a continuation of application No. 07/917,530, filed on Jul. 20, 1992, now abandoned, which is a continuation of application No. 07/742,471, filed on Aug. 2, 1991, now abandoned, which is a continuation of application No. 07/361,271, filed on Jun. 2, 1989, now abandoned.

(51) Int. Cl.$^7$ .................. A61K 39/395; A61K 39/40; A61K 39/42; C07K 16/00; C12P 21/08
(52) U.S. Cl. ..................... 424/130.1; 424/133.1; 424/137.1; 424/141.1; 424/144.1; 424/154.1; 530/388.1; 530/388.7; 530/388.73; 530/388.85
(58) Field of Search ............... 424/130.1, 133.1, 424/137.1, 141.1, 144.1, 154.1; 530/388.1, 388.7, 388.73, 388.85

(56) References Cited

U.S. PATENT DOCUMENTS 4,797,277   1/1989  Arfors .
5,091,513 * 2/1992  Huston et al. .
5,543,144 * 8/1996  Chang .

FOREIGN PATENT DOCUMENTS

WO 8904174  11/1988  (WO) .
WO 8806592   9/1998  (WO) .

OTHER PUBLICATIONS

Hildreth et al, J. Immunology 134; 3272–80, 1985.
Faley et al, Clin Exp. Immunol. 88:1–5, 1992.
Vedder et al, J. Clin. Invest. 81: 939–44, 1988.
Harris et al., Tibtech 11: 42–44, 1993.
Pastan et al, Coll 47: 641–648, 1986.
James E. Hildreth and Jennifer a. Hyman, Production and Characterization of Monoclonal Anti–CD–8 Anti–Idiotype Antibodies; Molecular Immunology, 26(12): 1155–1167, 1989.
McMichael Leucocyte Typing III Where Cell Differentiation Antigents, Oxford University Press, 1987, preface.
Ward et al, Therapeutic Immunology vol. 1: 165–171, 1994.
James E. Hildreth and J. Thomas August, The Human Lymphocyte Function–Associated (HLFA) Antigen and a Related macrophage Differentiation . . . ; The Journal of Immunology, 134(5): 3272–3280, 1985.
Corbi et al, Chromosomal Location of the Genes Encoding the Leukocyte Adhesion Receptors LFA–1, Mac–1 and p150,95, J.Exp.Med 167: pp. 1597–1607 (May 1988).
Dongworth et al (European Journal of Immunology vol. 15(9) pp. 888–892), 1985.*

* cited by examiner

*Primary Examiner*—Albert Navarro
(74) *Attorney, Agent, or Firm*—Gray Cary Ware & Freidenrich LLP; Lisa A. Haile

(57) ABSTRACT

Monoclonal antibodies and method for ameliorating an immune response disorder. The monoclonal antibodies are specific for an epitope present on the leukocyte adhesion receptor β-chain.

7 Claims, 3 Drawing Sheets

MONOCLONAL ANTIBODIES AGAINST LEUKOCYTE ADHESION RECEPTOR β-CHAIN, METHODS OF PRODUCING THESE ANTIBODIES AND USE THEREFOR

This application is a divisional of application Ser. No. 08/598,095, filed Feb. 7, 1996, now U.S. Pat. No. 5,888,508, which is a continuation of application Ser. No. 08/200,491, filed Feb. 22, 1994, now abandoned, which is a divisional application of U.S. patent application Ser. No. 08/063,063, filed May 20, 1993, now abandoned, which is a continuation of application Ser. No. 07/917,530, filed Jul. 20, 1992, now abandoned, which is a continuation of application Ser. No. 07/742,471, filed Aug. 2, 1991, now abandoned, which is a continuation of application Ser. No. 07/361,271, filed Jun. 2, 1989, now abandoned.

FIELD OF THE INVENTION

This invention relates to monoclonal antibodies specific for an epitope on the leukocyte adhesion receptor β-chain which can be used to suppress intercellular leukocyte adhesion.

DESCRIPTION OF THE BACKGROUND ART

Human immunodeficiency virus (HIV) is the etiologic agent of acquired immunodeficiency syndrome (AIDS), a fatal disease characterized by profound immunosuppression, opportunistic infections, and neuropathies. Although only a small fraction of circulating lymphocytes are infected with the virus, there is a marked loss of T cells bearing the virus receptor CD4. The depletion of $CD4^+$-T cells appears to contribute significantly to the immunosuppression associated with AIDS. Syncytium formation resulting from HIV-induced cell fusion has been shown to be the primary cytopathic effect of the virus in vitro and has been postulated to account for the loss of $CD4^+$-T cells in vivo. CD4 through its interaction with the HIV envelope glycoprotein gp120 plays an important role in syncytium formation.

Although the CD4 receptor appears to play a significant role in the etiology of AIDS, several observations suggest that molecules on the surface of uninfected cells other than CD4 are also involved in HIV-induced cell fusion. s First, fusion of HIV-infected cells to uninfected cells does not correlate with CD4-density on the surface of the uninfected cells. In addition, whereas transfection of non-lymphoid human cells with CD4 receptors renders such cells capable of fusion to HIV-infected cells, this is not true for CD4-transfected mouse cells. Finally, there is a disparity in the capacity of sera from AIDS patients to block binding of HIV particles to $CD4^+$-cells and the capacity of the same sera to block fusion of HIV-infected cells to $CD4^+$-uninfected cells.

CD4 interacts directly with class II major histocompatibility complex (MHC) molecules in class II MHC-restricted T helper cell responses. The involvement of the leukocyte adhesion receptor (LAR) LFA-1, in such responses has been demonstrated using anti-LFA-1 monoclonal antibodies (mAb). Structural similarities between gp120 and class II MHC suggested that the binding of gp120 to CD4 may mimic the interaction between class II MHC molecules and CD4. By analogy, the role of LAR in HIV-mediated cell fusion was examined. In the present invention, a mAb against LFA-1 completely inhibits HIV-mediated fusion of uninfected T cell blasts to HIV infected cells. This result indicates that LFA-1 is involved in HIV-induced syncytium formation, a major cytopathic mechanism of the virus.

The LFA-1 molecule, which is expressed on T and B lymphocytes as well as on macrophages, thymocytes, granulocytes, and a subpopulation of bone marrow cells, is composed of two non-covalently associated polypeptides of 175,000 Kd (α; CD11a) and 95,000 Kd (β; CD18). The β-chain of LFA-1 is also common to two other leukocyte antigens: Mac-1 (α-chain 165,000 Kd; CD11b); the type-three complement receptor; and LeuM5 (α-chain 150,000 Kd; CD11c), a molecule possibly associated with type-four complement receptor activity. Although the three α-subunits differ in size, there is evidence suggesting that all three subunits are encoded by a single gene or duplicated genes. cDNA encoding the human β-chain has been cloned and found to be 50% identical in primary structure to the β-chain of integrin, a chick fibroblast fibronectin receptor. These studies and others have shown that molecules of the LFA-1 glycoprotein family are members of the larger arginine-glycine-aspartate (RGD) adhesion family known as integrins.

At present, methods of limited effectiveness exist for the treatment of AIDS or other disorders in which the intercellular interaction of lymphocytes helps to mediate the pathologic state. Those drugs which are administered generally have severe contraindications associated with their use. Consequently, a considerable need exists for a therapeutic agent which can inhibit lymphocytic intercellular interaction in AIDS and other immune response mediated disorders.

SUMMARY OF THE INVENTION

One way to ameliorate immune response mediated disorders would be to suppress intercellular leukocyte adhesion using a monoclonal antibody which binds to a leukocyte adhesion receptor. In so doing, intercellular leukocyte binding is suppressed thereby decreasing the likelihood of cell-to-cell transmition of infectious agents and immune response activation.

In order to provide a means to ameliorate immune response mediated disorders, the inventor has developed monoclonal antibodies which bind to an epitope on the leukocyte adhesion receptor and suppresses the ability of leukocytes to adhere to each other. These monoclonal antibodies, if desired, can be therapeutically or diagnostically labelled.

DETAILED DESCRIPTION OF THE INVENTION

Figure 1:
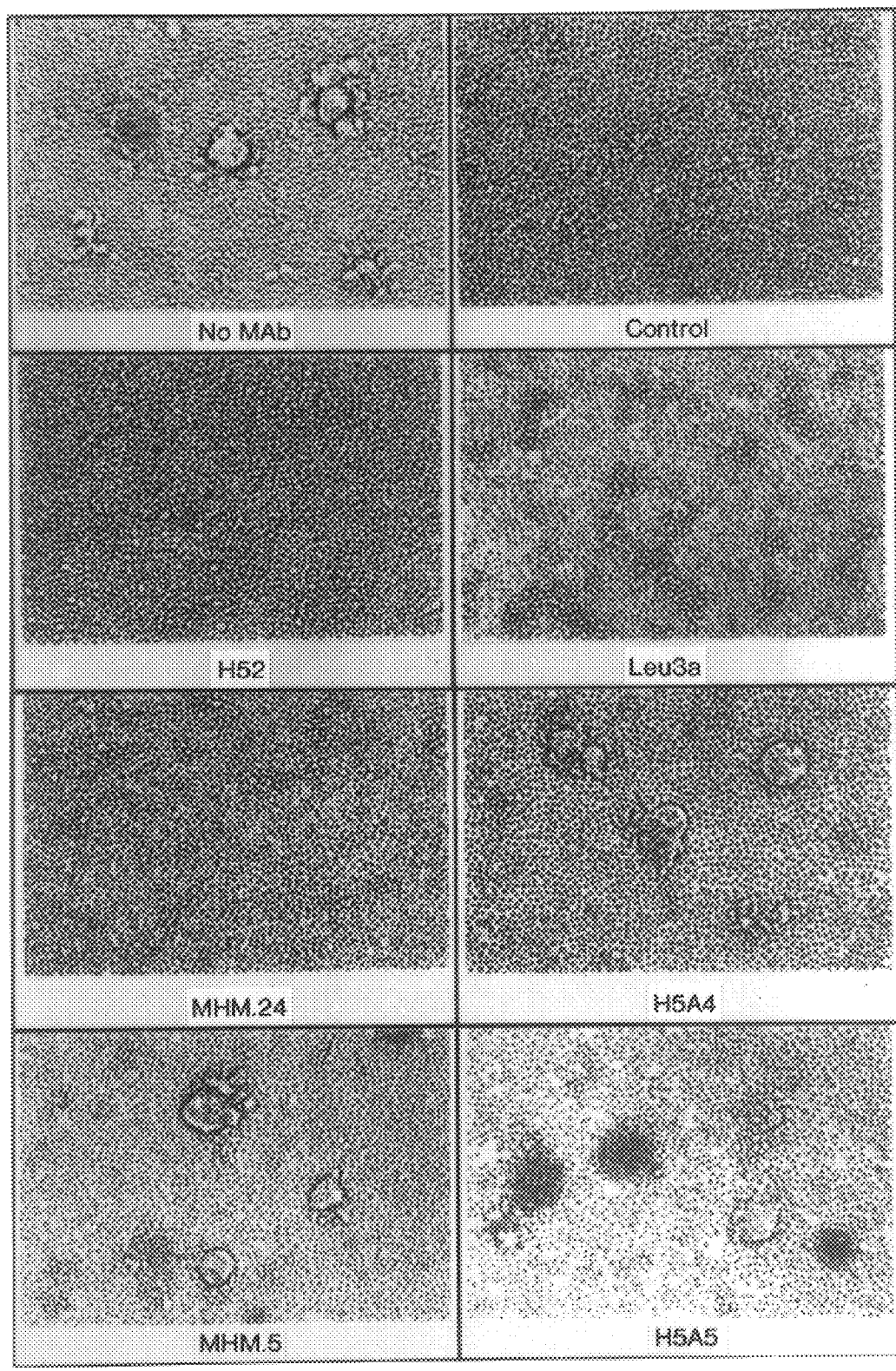
FIG. 1. Inhibition of syncytium formation by mAb.

The present invention relates to monoclonal antibodies with specificity for leukocyte adhesion receptor β-chain. These monoclonal antibodies are highly useful for both the in vitro and in vivo immunological detection of antigens having these β-chains and for immunotherapy of cells bearing these receptors having these β-chains.

In a preferred embodiment of the invention a monoclonal antibody (H52) is disclosed which binds to an epitope on the leukocyte adhesion receptor β-chain. This specificity enables H52, and like monoclonal antibodies with the specificity of H52, to be used to suppress intercellular adhesion. As a consequence, H52 is useful in ameliorating immune response mediated disorders such as AIDS, autoimmune disease, and graft, including graft versus host, rejection. H52 is obtained from, or has the identifying characteristics of, an antibody obtained from the cell line having ATCC accession number HB X. This cell line was placed on deposit for 30 years at the American Type Culture Collection (ATCC) in Rockville, Md. prior to Jun. 1, 1989.

Methods of Producing and Characterizing Monoclonal Antibodies

The general method used for production of hybridomas secreting monoclonal antibodies is well known (Kohler, et al., *European J. Imm.*, 6:292, 1976). Briefly, BALB/c mice were immunized with human splenic adherent cells and later boosted with the same type of cells. After 4 days, the animals were sacrificed and the spleen cells fused with mouse myeloma P3 X65 Ag8. Hybridomas were screened for antibody production and positive clones were tested for reactivity towards human spleen tissue sections.

The present invention is directed to monoclonal antibodies, and hybridomas which produce them, which are reactive with the leukocyte adhesion receptor β-chain.

The isolation of hybridomas secreting monoclonal antibodies with the reactivity of the monoclonal antibodies of the invention can be accomplished using routine screening techniques to determine the elementary reaction pattern of the monoclonal antibody of interest. Thus, if a monoclonal antibody being tested reacts with the leukocyte adhesion receptor β-chain such that intercellular adhesion is suppressed, then the antibody being tested and the antibody produced by the hybridomas of the invention are equivalent.

Alternatively, it is possible to evaluate, without undue experimentation, a monoclonal antibody to determine whether it has the same specificity as monoclonal antibody H52 of the invention by determining whether the monoclonal antibody being tested prevents H52 from binding to a particular antigen, for example the LFA-1 receptor with which H52 is normally reactive. If the monoclonal antibody being tested competes with H52, as shown by a decrease in binding by H52, then it is likely that the two monoclonal antibodies bind to the same epitope.

Still another way to determine whether a monoclonal antibody has the specificity of H52 is to pre-incubate H52 with an antigen with which it is normally reactive (for example, LFA-1 receptor), and determine if the monoclonal antibody being tested is inhibited in its ability to bind the antigen. If the monoclonal antibody being tested is inhibited then, in all likelihood, it has the same epitopic specificity as the monoclonal antibody of the invention.

While the in vivo use of a monoclonal antibody from a foreign donor species in a different host recipient species is usually uncomplicated, a potential problem which may arise is the appearance of an adverse immunological response by the host to antigenic determinants present on the donor antibody. In some instances, this adverse response can be so severe as to curtail the in vivo use of the donor antibody in the host. Further, the adverse host response may serve to hinder the intercellular adhesion-suppressing efficacy of the donor antibody. One way in which it is possible to circumvent the likelihood of an adverse immune response occurring in the host is by using chimeric antibodies (Sun, et al., *Hybridoma*, 5 (Supplement 1):S17, 1986; Oi, et al., *Bio Techniques*, 4(3):214, 1986). Chimeric antibodies are antibodies in which the various domains of the antibodies' heavy and light chains are coded for by DNA from more than one species. Typically, a chimeric antibody will comprise the variable domains of the heavy ($V_H$) and light ($V_L$) chains derived from the donor species producing the antibody of desired antigenic specificity, and the variable domains of the heavy ($C_H$) and light ($C_L$) chains derived from the host recipient species. It is believed that by reducing the exposure of the host immune system to the antigenic determinants of the donor antibody domains, especially those in the $C_H$ region, the possibility of an adverse immunological response occurring in the recipient species will be reduced. Thus, for example, it is possible to produce a chimeric antibody for in vivo clinical use in humans which comprises mouse $V_H$ and $V_L$ domains coded for by DNA isolated from ATCC HB X, and $C_H$ and $C_L$ domains coded for with DNA isolated from a human leukocyte.

Under certain circumstances, monoclonal antibodies of one isotype might be more preferable than those of another in terms of their diagnostic or therapeutic efficacy. For example, from studies on antibody-mediated cytolysis, it is known that unmodified mouse monoclonal antibodies of isotype gamma-2a and gamma-3 are generally more effective in lysing target cells than are antibodies of the gamma-1 isotype. This differential efficacy is thought to be due to the ability of the gamma-2a and gamma-3 isotypes to more actively participate in the cytolytic destruction of target cells. Particular isotypes of a monoclonal antibody can be prepared either directly, by selecting from the initial fusion, or prepared secondarily, from a parental hybridoma secreting a monoclonal antibody of different isotype by using the sib selection technique to isolate class-switch variants (Steplewski, et al., *Proceedings of the National academy of Science, U.S.A.*, 82:8653, 1985; Spira, et al., *Journal of Immunological Methods*, 74:307, 1984). Thus, the monoclonal antibodies of the invention would include class-switch variants having the specificity of monoclonal antibody H52 which is produced by ATCC HB X.

When the monoclonal antibodies of the invention are used in the form of fragments, such as, for example, Fab and F(ab')$_2$, and especially when these fragments are therapeutically labeled, any isotype can be used since amelioration of the immune response disorders in these situations is not dependent upon complement-mediated cytolytic destruction of those cells bearing the leukocyte adhesion receptor.

The term "immune response mediated disorder" denotes disorders in which the hosts' immune system contributes to the disease condition either directly or indirectly. Examples of disorders which are mediated by the immune response includes AIDS, autoimmune disease, and graft rejection. As used herein, graft rejection encompasses both host versus graft and graft versus host rejection.

The monoclonal antibodies of the invention can be used in any animal in which it is desirable to administer in vitro or in vivo immunodiagnosis or immunotherapy. The term "animal" as used herein is meant to include both humans as well as non-humans.

The term "antibody" as used in this invention is meant to include intact molecules as well as fragments thereof, such as, for example, Fab and F(ab')$_2$, which are capable of binding the epitopic determinant.

Diagnostic Uses

The monoclonal antibodies of the invention are suited for use in immunoassays in which they can be utilized in liquid phase or bound to a solid phase carrier. In addition, the monoclonal antibodies in these immunoassays can be detectably labeled in various ways. Examples of types of immunoassays which can utilize monoclonal antibodies of the invention are competitive and non-competitive immunoassays in either a direct or indirect format. Examples of such immunoassays are the radioimmunoassay (RIA) and the sandwich (immunometric) assay. Detection of the antigens using the monoclonal antibodies of the invention can be done utilizing immunoassays which are run in either the forward, reverse, or simultaneous modes, including immunohistochemical assays on physiological samples.

The monoclonal antibodies of the invention can be bound to many different carriers and used to detect the presence of leukocyte adhesion factor. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, chemiluminescent compounds, and bioluminescent compounds. Those of ordinary skill in the art will know of other suitable labels for binding to the monoclonal antibody, or will be able to ascertain such, using routine experimentation. Furthermore, the binding of these labels to the monoclonal antibody of the invention can be done using standard techniques common to those of ordinary skill in the art.

For purposes of the invention, the leukocyte adhesion factor β-chain which is detected by the monoclonal antibodies of the invention may be present in biological fluids and tissues. Any sample containing a detectable amount of leukocyte adhesion factor β-chain can be used. Normally, a sample is a liquid such as urine, saliva, cerebrospinal fluid, blood, serum and the like, or a solid or semi-solid such as tissues, feces, and the like.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, pyridoxal, and fluorescein, which can react with specific anti-hapten antibodies.

As used in this invention, the term "epitope" is meant to include any determinant capable of specific interaction with the monoclonal antibodies of the invention. Epitopic determinants usually consist of chemically active surface groupings of molecules such as amino acids or sugar side chains and usually have specific three dimensional structural characteristics, as well as specific charge characteristics.

In using the monoclonal antibodies of the invention for the in vivo detection of antigen, the detectably labeled monoclonal antibody is given in a dose which is diagnostically effective. The term "diagnostically effective" means that the amount of detectably labeled monoclonal antibody is administered in sufficient quantity to enable detection of the site having the leukocyte adhesion receptor β-chain for which the monoclonal antibodies are specific.

The concentration of detectably labeled monoclonal antibody which is administered should be sufficient such that the binding to those cells having leukocyte adhesion receptor is detectable compared to the background signal. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex and extent of disease of the individual. The dosage of monoclonal antibody can vary from about 0.01 mg/m$^2$ to about 20 mg/m$^2$, preferably about 0.1 mg/m$^2$ to about 10 mg/m$^2$.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 keV range, which may be readily detected by conventional gamma cameras.

For in vivo diagnosis radioisotopes may be bound to immunoglobin either directly or indirectly by using an intermediate functional group. Intermediate functional groups which often are used to bind radioisotopes which exist as metallic ions to immunoglobins are the bi-functional chelating agents such as diethylenetriaminepentacetic acid (DTPA) and ethylenediaminetetraacetic acid (EDTA) and similar molecules.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI.

The monoclonal antibodies of the invention can be used to monitor the course of amelioration of an immune response mediated disorder in an individual. Thus, by measuring the increase or decrease in the number of leukocytes or changes in the concentration of antigen shed into various body fluids, it would be possible to determine whether a particular therapeutic regimen aimed at ameliorating the immune response mediated disorder is effective.

Therapeutic Uses

The term "ameliorate" denotes a lessening of the detrimental affect of the immune response mediated disorder in the animal receiving therapy. The term "therapeutically effective" means that the amount of monoclonal antibody used is of sufficient quantity to ameliorate the cause of disease due to the immune response.

The monoclonal antibodies of the invention can also be used for immunotherapy in an animal having an immune response mediated disorder caused by leukocytes which express leukocyte adhesion receptor β-chain with epitopes reactive with the monoclonal antibodies of the invention. When used in this manner, the dosage of monoclonal antibody can vary from about 10 mg/m$^2$ to about 2000 mg/m$^2$.

When used for immunotherapy, the monoclonal antibodies of the invention may be unlabeled or labeled with a therapeutic agent. These agents can be coupled either directly or indirectly to the monoclonal antibodies of the invention. One example of indirect coupling is by use of a spacer moiety. These spacer moieties, in turn, can be either insoluble or soluble (Diener, et al., *Science*, 231:148, 1986) and can be selected to enable drug release from the monoclonal antibody molecule at the target site. Examples of therapeutic agents which can be coupled to the monoclonal antibodies of the invention for immunotherapy are drugs, radioisotopes, lectins, and toxins.

The drugs with which can be conjugated to the monoclonal antibodies of the invention include compounds which are classically referred to as drugs such as for example, mitomycin C, daunorubicin, and vinblastine.

In using radioisotopically conjugated monoclonal antibodies of the invention for immunotherapy certain isotypes may be more preferable than others depending on such factors as leukocyte distribution as well as isotype stability and emission. If desired, the leukocyte distribution can be evaluated by the in vivo diagnostic techniques described above. Depending on the immune response mediated disorder some emitters may be preferable to other. In general, alpha and beta particle-emitting radioisotopes are preferred in immunotherapy. Preferred are short range, high energy alpha emitters such as $^{212}$Bi. Examples of radioisotopes which can be bound to the monoclonal antibodies of the invention for therapeutic purposes are $^{125}$I, $^{131}$I, $^{90}$Y, $^{67}$Cu, $^{212}$Bi, $^{211}$At, $^{212}$Pb, $^{47}$Sc, $^{109}$Pd and $^{188}$Re.

Lectins are proteins, usually isolated from plant material, which bind to specific sugar moieties. Many lectins are also able to agglutinate cells and stimulate lymphocytes. However, ricin is a toxic lectin which has been used immunotherapeutically. This is accomplished by binding the alpha-peptide chain of ricin, which is responsible for toxicity, to the antibody molecule to enable site specific delivery of the toxic effect.

Toxins are poisonous substances produced by plants, animals, or microorganisms that, in sufficient dose, are often lethal. Diphtheria toxin is a substance produced by *Corynebacterium diphtheria* which can be used therapeutically. This toxin consists of an alpha and beta subunit which under proper conditions can be separated. The toxic A component can be bound to an antibody and used for site specific delivery to a leukocyte expressing leukocyte adhesion factor β-chain for which the monoclonal antibodies of the invention are specific.

Other therapeutic agents which can be coupled to the monoclonal antibodies of the invention are known, or can be easily ascertained, by those of ordinary skill in the art.

The dosage ranges for the administration of the monoclonal antibodies of the invention are those large enough to produce the desired effect in which the symptoms of the immune response mediated disorder are ameliorated. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications. Dosage can vary from about 0.1 mg/m$^2$ to about 2000 mg$^2$/m, preferably about 0.1 mg/m$^2$ to about 500 mg/m$^2$/dose, in one or more dose administrations daily, for one or several days.

Generally, when the monoclonal antibodies of the invention are administered conjugated with therapeutic agents lower dosages, as compared those used for in vivo immunodiagnostic imaging, can be used.

The monoclonal antibodies of the invention can be administered parenterally by injection or by gradual perfusion over time. The monoclonal antibodies of the invention can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The invention also relates to a method for preparing a medicament or pharmaceutical composition comprising the monoclonal antibodies of the invention, the medicament being used for therapy of immune response mediated disorders due to leukocytes expressing leukocyte adhesion receptor β-chain reactive with the monoclonal antibodies of the invention.

The above disclosure generally describes the present invention. A more complete understanding can be obtained by reference to the following specific examples which are provided herein for purposes of illustration only, and are not intended to limit the scope of the invention.

EXAMPLE 1

PREPARATION OF ANTIADHESION MONOCLONAL FACTOR ANTIBODIES

Female Balb/c mice (6 to 8 weeks old) were injected intraperitoneally with 10$^7$ human splenic adherent cells in phosphate buffered saline. This treatment was repeated after 14 days and again after 21 days. Four days after the final injection the spleen was removed from one of the immunized mice and a single cell suspension prepared. The splenic cells were fused to Balb/c derived P3×653.Ag8 myeloma cells with 50% polyethylene glycol after the method of Kohler and Milstein (Nature:256:495, 1976). After establishing growing hybridoma colonies, supernatants from these cells were tested for antibodies against human antigens by immunohistochemistry on cryostat sections (4μ) of frozen human spleens (Naiem, et al., *J. Immun. Meth.*, 50:145, 1982). H52 (H52.G1.2) was selected for cloning and re-cloning by immunohistochemistry, radioimmunoassays on human cells, and by radioimmunoprecipitation from human cells.

EXAMPLE 2

INHIBITION OF SYNCYTIUM FORMATION BY MONOCLONAL ANTIBODY

The effect of mAb on the fusion of 8E5 cells to PHA-blasts was determined in a syncytium formation assay. The 8E5 and A3.01 cell lines were maintained in complete medium (RPMI-1640 supplemented with 10% FBS (HyClone) and 10 mM HEPES). The 8E5 cell line is a surviving clone of A.301 cells infected with LAV. 8E5 cells carry a single copy of the entire LAV genome but produce non-infectious virus particles due to a point mutation in the reverse transcriptase gene. 8E5 cells express HIV envelope glycoproteins and when mixed with CD4-positive PHA-blasts and T cell lines produce cytopathic effects identical to those observed in cultures of T cells infected with wild-type virus.

PHA-blasts were generated by incubating peripheral blood mononuclear cells for 3 days in the presence of PHA (Wellcome Diagnostics) at a concentration of 0.25 μg/ml in complete medium. Cells were washed 3 times with PBS and resuspended in complete medium at a density of 5×10$^6$/ml. MAb were used in the form of purified IgG at a concentration of 25 μg/ml. PHA-blasts were mixed with an equal volume (30 μl) of monoclonal antibody or medium in the wells of half-area 96-well plates (Costar) and incubated for 30 minutes at 25° C. Thirty μl of 8E5 cells were then added followed by incubation for 10 hr at 37° C. in a humidified $CO_2$ incubator. Control wells consisted of PHA-blasts incubated with an equal number of uninfected A.301 cells. In the assay, syncytia or balloon cells consisting of 10 to 50 or more fused cells form within 4 and 10 hours after mixing 8E5 cells with PHA blasts and $CD4^+$ T cell lines, respectively. Continued incubation results in rapid syncytia death as determined by vital dye exclusion.

To determine their effect on HIV-mediated cell fusion mAb against human leukocyte antigens were added to co-cultures of PHA-blasts and 8E5 cells. The mAb tested were: H52, anti-CD18 (LFA-1 β); MHM.24, anti-CD11a (LFA-1 α); H5A4, anti-CD11b (Mac-1 α); H5A5, anti-CD45 (leukocyte common antigen); MHM.5, anti-HLA-A, B,C; Leu3a, anti-CD4. All antibodies are IgG1,k isotype.

As shown in FIG. 1, H52, against an epitope on the β-submit of LFA-1 (CD 18), completely inhibited syncytium formation. Fusion was also blocked by a mAb (MHM.24) against the α-subunit of LFA-1 (CD11a). However, the mAb MHM.24 was less effective than mAb H52 since very small syncytia were rarely observed. H5A4, a mAb against a different member of the LAR family, Mac-1 (complement receptor type-3; CD11b), had no effect on the fusion of 8E5 cells to the PHA blasts. Also, fusion was not affected by two mAb recognizing unrelated cell surface proteins: MHM.5, anti-HLA-A,B,C, and H5A5, anti-leukocyte common antigen (CD45). Since these two antigens are expressed at equal or higher densities than LAR on PHA blasts, the failure of the latter two antibodies to block fusion suggests that inhibition by anti-LAR antibodies was not due to a non-specific steric effect. Leu3a, a mAb against CD4, which has been previously shown to block binding of gp120 to CD4, completely inhibited fusion of 8E5 to PHA-blasts (FIG. 1). Inhibition of fusion by Leu3a and the absence of fusion between the PHA-blasts and uninfected A.301 cells (FIG. 1, control) confirmed that the fusion was mediated by HIV. A number of commercially available mAb against gp120 failed to inhibit fusion in the assay system. PHA-blasts and the 8E5 cells formed very large aggregates within 1 hr of mixing in the syncytium assay. These aggregates were completely inhibited by H52, MHM.24, and Leu3a, but not by the other mAb. The inhibition of syncytium formation by mAb H52 was observed whether the PHA blasts were mixed with 8E5 cells infected with the mutant virus or the CEM T cell line infected with wild type HIV (HTLV-IIIB).

EXAMPLE 3

INHIBITION OF SYNCYTIUM FORMATION BY H52

PHA-blasts, generated as described in Example 1, were incubated with various concentrations of purified H52 or PLM-2 IgG before adding 8E5 cells. PLM-2 is an IgG1,k mAb against CD18 which does not inhibit LFA-1-mediated functions. The assay was carried out exactly as described in Example 1. Syncytia were counted on an inverted microscope using a low power objective (40×) after adding trypan blue (0.1%). Data shown in FIG. 2 are the mean syncytia count/$10^6$ 8E5 cells of duplicate wells.

Figure 2:
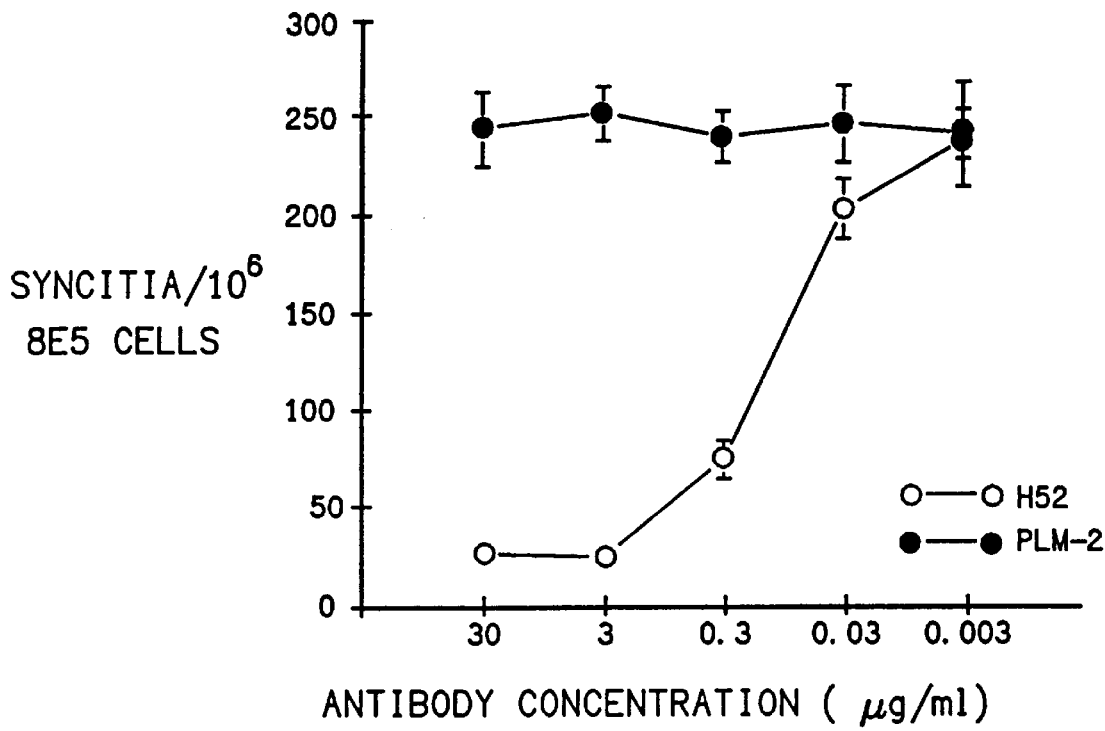
FIG. 2. Dose dependent inhibition of syncytium formation by H52 IgG.

The H52 mAb blocked 8E5-PHA-blast fusion in a dose-dependent manner with complete inhibition observed at concentrations above 3 μg/ml (FIG. 2). The inhibition of LFA-1-mediated lymphocyte adhesion functions by mAb H52 shows a very similar dose-dependency. PLM-2, a mAb against a CD18 epitope not associated with LFA-1 adhesion functions, did not affect fusion at any concentration (FIG. 2).

Studies were also done to determine the level at which fusion was blocked by H52. PHA-blasts and 8E5 cells ($2.5 \times 10^6$) were incubated for 1 hr on ice in 0.5 ml of complete medium alone or complete medium containing purified H52 or PLM-2 IgG at 25 μg/ml. After pelleting the cells, unbound mAb was removed by washing 2 times with 10 ml of PBS. The antibody-coated PHA blasts, and 8E5 cells were then resuspended in complete medium and mixed with uncoated 8E5 cells and PHA blasts, respectively, followed by incubation at 37° C. for 10 hr as described in Example 1. Syncytia formation was scored as described above.

Previous studies have shown that inhibition of lymphocyte interactions by anti-LFA-1 antibodies is a uni-directional effect even when both cell types express LFA-1. To determine if the effect of anti-LFA-1 mAb on syncytium formation was also uni-directional, LFA-1 expression was analyzed by flow cytometry. Both 8E5 cells and PHA-blasts expressed LFA-1, although the expression on 8E5 was substantially less than on the blasts.

Figure 3:
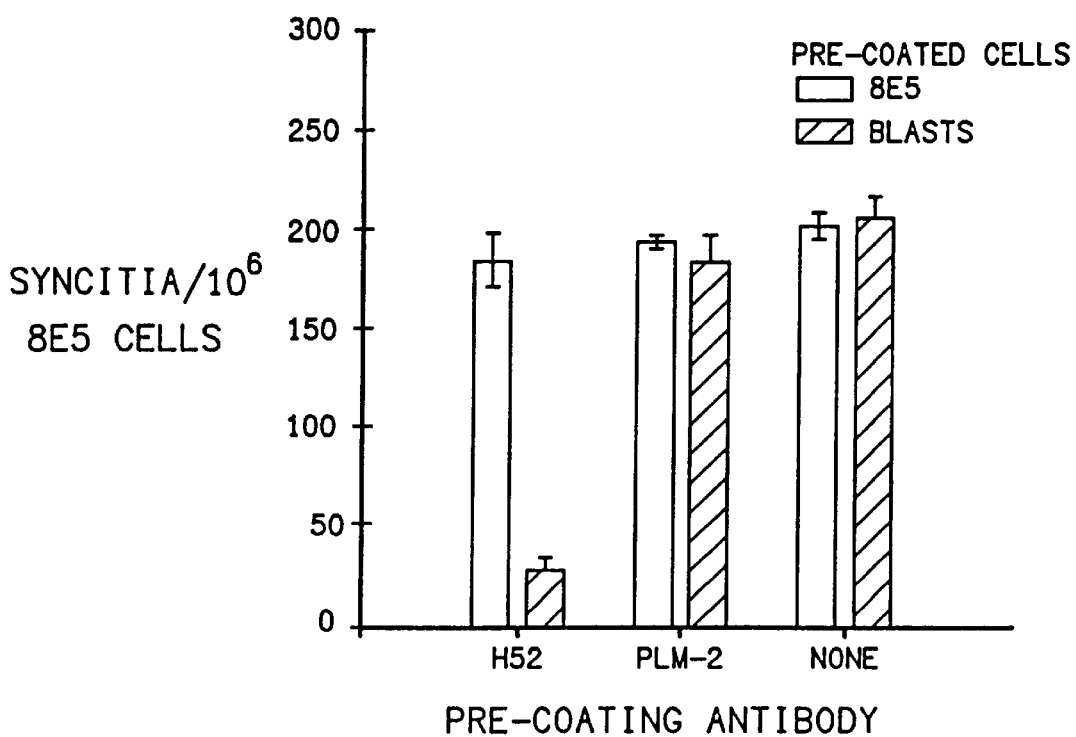
FIG. 3. H52 blocks syncytia formation at the level of PHA-blasts not 8E5 cells.

Each cell type was pre-coated with mAb H52 or the control mAb PLM-2 and washed to remove unbound mAb before assaying syncytium formation. Pre-coating PHA-blasts with H52 resulted in near complete inhibition of fusion while similar treatment of the 8E5 cells had no effect (FIG. 3). Fusion was not affected by pre-coating either the PHA-blasts or the 8E5 cells with the control mAb. This result showed that the anti-LFA-1 antibody blocked fusion at the level of the PHA-blast and not the HIV-infected 8E5 cells. This suggests that LAR on the $CD4^+$ cells interacted with a ligand expressed on 8E5 cells.

EXAMPLE 4

INHIBITION OF HIV gp120 BINDING BY H52

Non-specific agents such as dextran sulfate that block the interaction of HIV envelope glycoprotein gp120 with CD4 by steric effects are known to inhibit HIV-mediated cell-cell fusion. Consequently, the binding of mAb H52 to LFA-1 on the surface of $CD4^+$-cells was tested to determine whether H52 interfered with the binding of gp120 to CD4.

Figure 4:
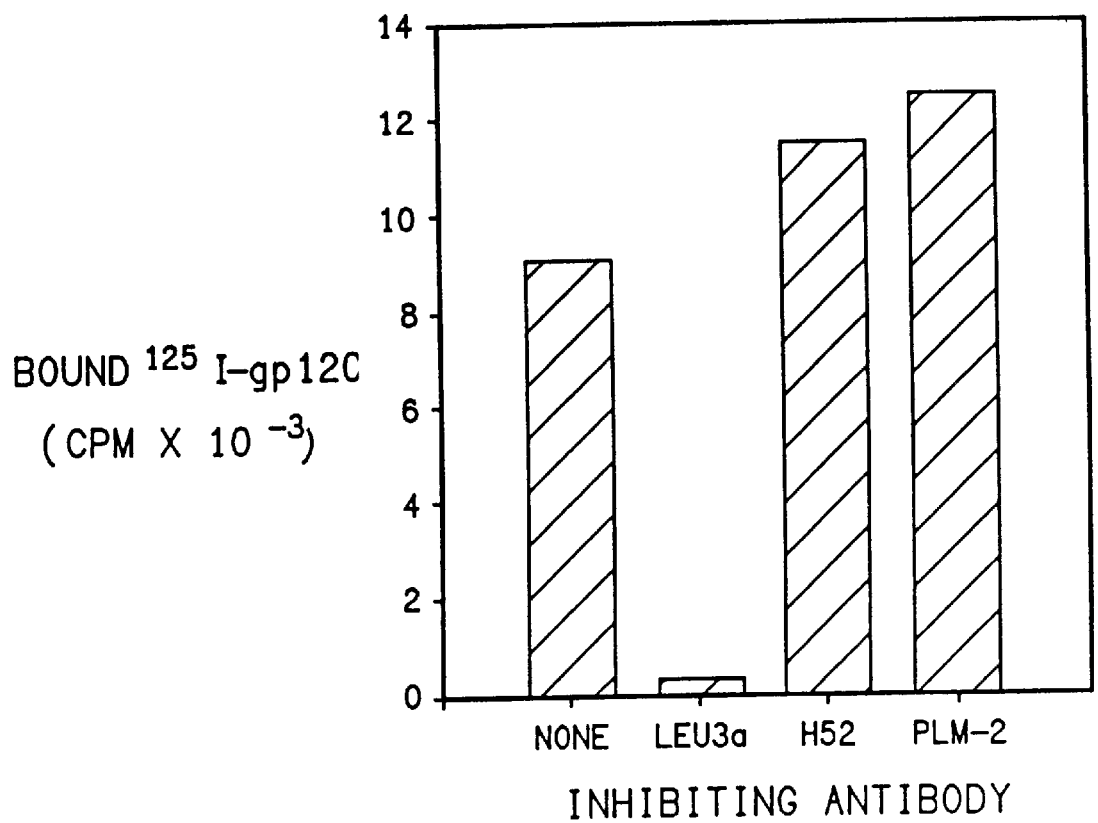
FIG. 4. Inhibition of gp120 binding to CEM cells by mAb.

To purify gp120, HIV was pelleted (110,000×g, 1.5 hr) from culture supernatants of infected PHA-blasts cells and washed once with PBS. The virus was resuspended in PBS and vortexed vigorously to shear off gp120, followed by centrifugation at 110,000×g. The resulting supernatant was concentrated using a 30,000 dalton cut-off Centricon filter. The retained proteins, which consisted primarily of gp120 and bovine serum albumin (BSA; 10 to 30%), were radio-iodinated using the standard chloramine-T method. The labeled proteins (2 to 5 μCi/g) were diluted in PBS containing a high concentration of BSA (2%) to eliminate binding of $^{125}$I-BSA. $CD4^+$-CEM cells ($5 \times 10^5$) were pre-incubated with Leu3a, H52, and PLM-2 mAb at 25 g/ml in complete medium (see Example 1) before adding 50 ng of radioiodinated gp120. Following a 1 hr incubation at 0° C. the cells were washed twice and bound radiolabel measured. Background binding was determined by preincubating cells with a 200-fold excess of unlabeled gp120. Consistent with previous findings, cells pre-coated with the Leu3 a mAb (anti-CD4) did not bind gp120 (FIG. 4). In contrast, pre-coating cells with either mAb H52 or the control mAb PLM-2 had no inhibitory effect on the binding of gp120. This result demonstrated that inhibition of syncytium formation by mAb H52 was not due to interference with HIV receptor function since binding of gp120 to CD4 was not blocked by this mAb.

The invention now being fully described, it will be apparent to one of ordinary skill in the art that many changes and modifications can be made without departing from the spirit or scope of the invention.

What is claimed is:

1. An antibody or antigen binding fragment thereof having binding specificity of the antibody produced by ATCC HB 10160 for a leukocyte adhesion receptor β-chain, said antibody having a light chain or heavy chain coded for by DNA from more than one species.

2. The antibody of claim 1, wherein the fragment is selected from the group consisting of Fab and F(ab')2.

3. The antibody of claim 2, wherein the fragment is F(ab')2.

4. The antibody of claim 1, wherein the antibody has isotype gamma-2a.

5. The antibody of claim 1, wherein the antibody competes with the antibody produced by ATCC HB 10160 for binding to LFA-1.

6. The antibody of claim 1, wherein binding of the antibody to LFA-1 is inhibited by pre-incubation of LFA-1 with the antibody produced by ATCC HB 10160.

7. A composition for treatment of an immune response-mediated disorder, comprising the antibody of claim 1 and a carrier.

* * * * *